United States Patent [19]

Yoshida et al.

[11] Patent Number: 4,708,940
[45] Date of Patent: Nov. 24, 1987

[54] METHOD AND APPARATUS FOR CLINICAL ANALYSIS

[75] Inventors: Kasumi Yoshida, Mito; Nobuyoshi Takano; Naoya Ono, both of Katsuta, all of Japan

[73] Assignee: Hitachi, Ltd., Tokyo, Japan

[21] Appl. No.: 473,867

[22] Filed: Mar. 10, 1983

[30] Foreign Application Priority Data

Mar. 10, 1982 [JP] Japan ................ 57-36462

[51] Int. Cl.⁴ ............... G01N 21/07; G01N 21/11; G01N 37/00
[52] U.S. Cl. ..................... 436/45; 422/72; 422/100
[58] Field of Search ........ 422/72, 64, 67, 73, 422/100; 436/45; 494/16, 17, 42, 56, 57

[56] References Cited

U.S. PATENT DOCUMENTS

| | | | |
|---|---|---|---|
| 3,081,158 | 3/1963 | Winter | 494/17 |
| 3,679,129 | 7/1972 | Livshitz et al. | 422/72 |
| 3,801,283 | 4/1974 | Shapiro et al. | 422/72 |
| 3,985,508 | 10/1976 | Williams | 422/65 |
| 4,054,415 | 10/1977 | Seligson et al. | 422/64 |
| 4,104,026 | 8/1978 | Brooker et al. | 422/64 |
| 4,208,484 | 6/1980 | Sogi et al. | 422/72 |
| 4,225,558 | 9/1980 | Peterson et al. | 422/72 |
| 4,276,260 | 6/1981 | Drbal et al. | 422/100 |
| 4,311,394 | 1/1982 | Manobe | 422/64 |
| 4,338,279 | 7/1982 | Orimo et al. | 422/67 |
| 4,343,709 | 8/1982 | Okumura | 494/17 |
| 4,381,072 | 4/1983 | Matsumoto | 422/72 |
| 4,547,340 | 10/1985 | Sanuki et al. | 422/64 |

*Primary Examiner*—Michael S. Marcus
*Attorney, Agent, or Firm*—Antonelli, Terry & Wands

[57] ABSTRACT

A clinical analyzer with an analyzing section having a reaction tube and photometer, and a sampling section having a sample transfer pipe and centrifugal separator which also serves as a sampler. Sample containers containing blood are set on a plurality of container holders through an aperture formed in the cover of the centrifugal separator. A rotor with the container holders mounted thereon is rotated at a low speed intermittently so that each of the container holders is positioned at the container setting position in a predetermined order in which a container holder which is not located adjacently to the previously positioned container holder is positioned next.

Subsequently, the rotor is rotated at a high speed for a predetermined period so that the sample liquid in each sample container centrifugally separated. After the centrifugal separation, the rotor is rotated at a low speed intermittently so that the sample containers set on the container holders are positioned to the sample take-out position in the same order as in setting the sample containers. A pipe is inserted through a sample transfer hole formed in the cover of the centrifugal separator into the sample container, and the sample liquid is pumped up and transported to the analyzing section. This series of operations is repeated and a plurality of samples are measured for items of analysis by the photometer sequentially.

23 Claims, 7 Drawing Figures

F I G. 1
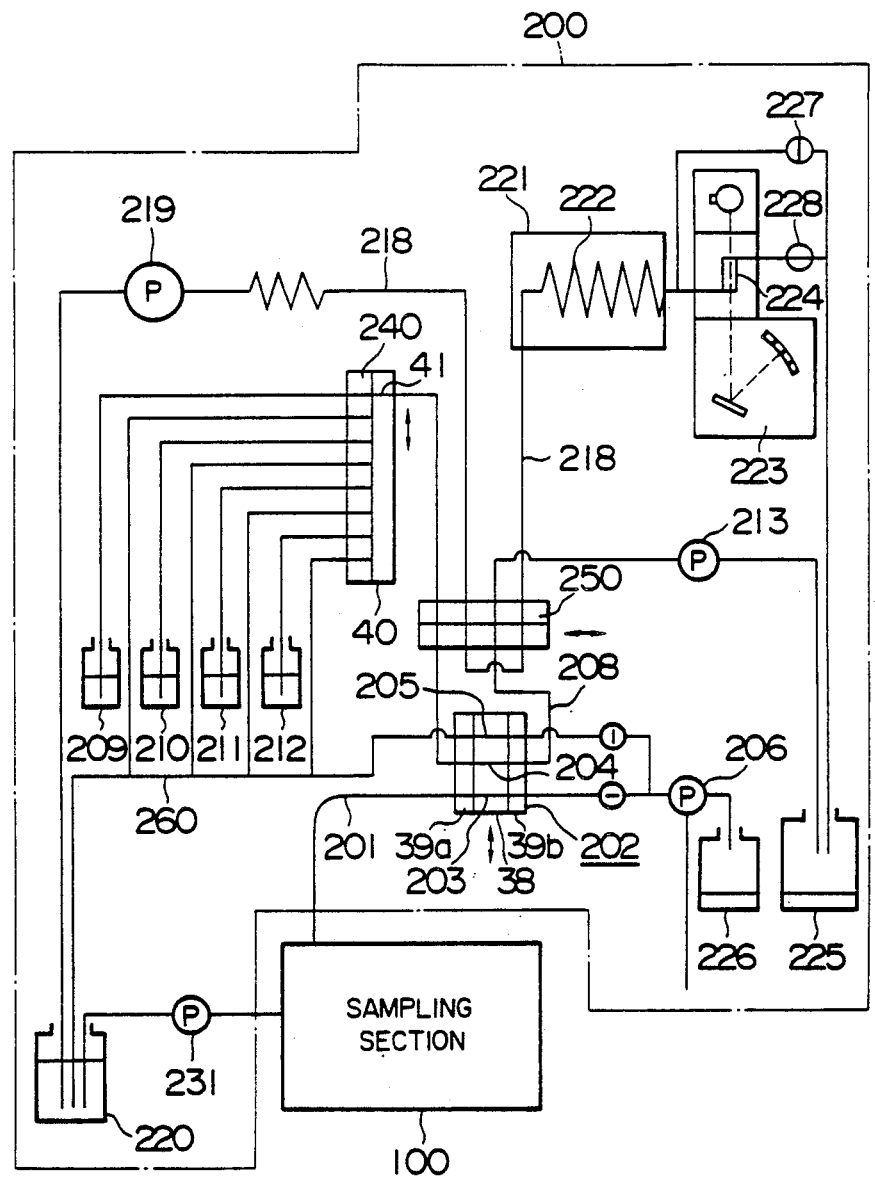

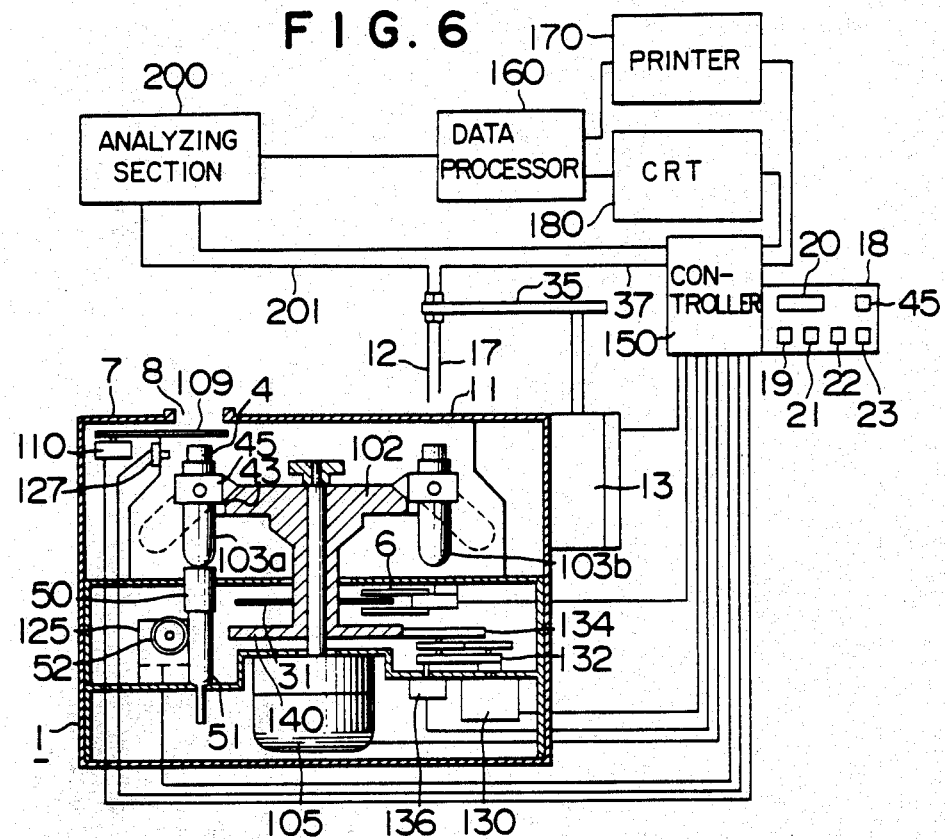

METHOD AND APPARATUS FOR CLINICAL ANALYSIS

The present invention relates to a method and apparatus for analyzing body fluid such as blood and, more particularly, to a method and apparatus for analyzing the composition of blood plasma or blood serum which have been separated centrifugally from blood of a patient in a hospital.

In hospitals, the chemical examination for analyzing the chemical composition of blood of patients is indispensable for diagnosing the sickness of the patients, and it has a large number of samples and items of analysis. Therefore, there are many advanced chemical analyzers.

Since the advent of the continuous flow analysis as disclosed, for example, in U.S. Pat. No. 4,315,754, the analyzing time has become shorter. However, it still takes a long time in the whole process beginning with the reception of a patient and ending with the determination based on the examination. According to the common procedures as a preprocessing for sampling blood serum or blood plasma, a large number of samples are gathered, and then each sample blood is separated centrifugally in one examination room, the separated sample is transported to another examination room, then it is set on the automatic analyzer. The clinical examiner sets the gathered samples on the centrifugal separator one by one, and after all samples have been processed, samples of blood plasma in many centrifugal tubes are transferred into many sample pots or containers for the automatic analyzer. This preprocessing before setting samples on the automatic clinical analyzer is a tedious and time-consuming task.

It is an object of the present invention to provide a method and apparatus for analyzing body fluid, wherein the sampler of the analyzer is provided with a centrifugally separation function.

Another object of the present invention is to provide a method and apparatus for analyzing blood, wherein blood samples can be handled efficiently so as to save the operator's job.

Still another object of the present invention is to provide a method and apparatus for processing a small number of samples promptly.

Further object of the present invention is to provide a method and apparatus for clinical analysis, wherein a series of operations from preprocessing to display for the result of analysis are carried out automatically.

The inventive analyzer has a sampling section and an analyzing section. The analyzing section performs measuring operations in accordance with items of analysis, while the sampling section has a function for separating centrifugally a plurality of body liquid samples and function for collecting and transferring the supernatant liquid into the analyzing section.

According to a preferred embodiment of the present invention, the rotor of the centrifugal separator is moved so that it passes by the sample pot or container setting position and the sample transfer position. The rotor moves intermittently at a low speed before the centrifugal separating operation so as to place pot holders attached on the rotor at the pot setting position one by one. During the separating operation, the rotor rotates at a high speed. After the separating operation, the rotor is moved again intermittently at a low speed, and at this time pot holders with sample pots mounted thereon are positioned at the sample transfer position one by one. While each sample pot is placed at the sample transfer position in the centrifugal separator, the liquid suction pipe is put into the sample liquid, and a certain amount of sample liquid is pumped up.

The present invention will be apparent from the following detailed description taken in conjunction with the accompanying drawings, in which:

FIGS. 1 through 5 are illustrations explaining one embodiment of the present invention. Individually, FIG. 1 is a systematic diagram showing the relationship between the sampling section and the analyzing section;

FIG. 2 is a partial cross-sectional view showing in brief the structure of the sampling section;

FIG. 3 is a plan view showing in brief the sampling section during the cleaning process for the suction pipe;

FIG. 4 is an illustration explaining the state of the rotor during the centrifugal separating operation;

FIG. 5 is an illustration explaining the state of the rotor during the sample pot setting operation.

FIGS. 6 and 7 are illustrations explaining another embodiment of the present invention, where FIG. 6 is a brief structural diagram showing mainly the sampling section of the apparatus; and FIG. 7 is a plan view showing, partly broken way, the structure of the centrifugal separator.

Figure 2:
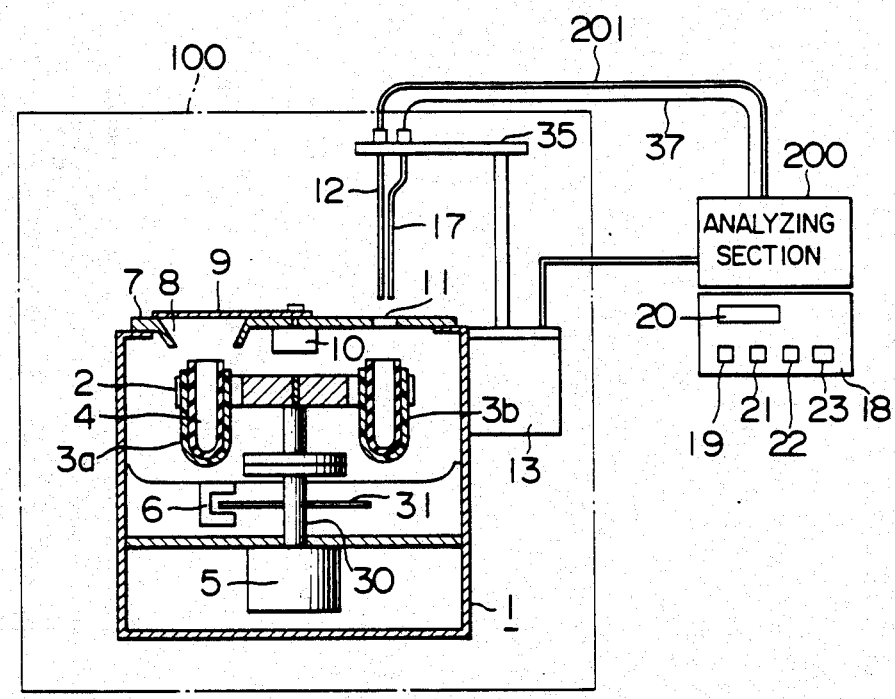

In the embodiment of FIG. 1, the present invention is applied to a continuous flow analyzer, wherein the analyzer is made up of a sampling section 100 and an analyzing section 200. The sampling section 100 performs centrifugal separation for the blood sample, and the composition of the supernatant liquid is measured by the analyzing section 200. The sampler of the sampling section has a function of centrifugal separation.

In this embodiment, the lid of the centrifugal chamber is kept closed normally, but is provided with a sample pot transfer port through which a test tube for each sample is transferred and a sample transfer port through which the separated sample is introduced to the analyzer.

The centrifugal machine has a function for separating blood by rotating at a high speed and a function for positioning the rotor at arbitrary positions by rotating intermittently at a low speed. For setting a sample, the rotor rotates automatically to receive a sample pot on a holder having specified number, and after the sample has been separated, the rotor rotates again automatically so that the sample pot is positioned at the sample transfer port where the sample is pumped up to the analyzer. The position of each pot holder is checked by the position sensors.

For setting a sample pot to be processed, the rotor rotates so that the sample pot is inserted at a location specified by the apparatus. For example, when only one sample is processed, a sample pot is inserted in pot holder No. 1, and after the separating process the sample pot is turned to the sample transfer port and the sample is introduced to the analyzer. In this case, pot holders on the rotor are numbered such that a pair of an odd number and the next larger even number, such as No. 1 and No. 2, or No. 3 and No. 4, are located symmetrically with respect to the center of the rotor, so that when a plurality of samples are processed, sample pots are inserted in numerical order thereby to balance the rotor irrespective of the number of test pots mounted. Processed samples are introduced to the analyzer in the same order.

The sample is introduced into the analyzer by pumping the necessary amount of liquid sample through the transfer pipe provided at the sample transfer section. After the pumping operation, the centrifugal machine is immediately ready to receive the next samples. For the analysis of multiple components, the sample introduced into the sample transfer pipe is partitioned into several portions and they are introduced sequentially into the measuring tube provided on the sampling valve at a constant time interval. In synchronization with this operation, reagents which have been prepared in the reagent reservoir are introduced into the reagent transfer pipe provided on the reagent transfer valve in the order of times of analysis.

The liquid pump transfers the carrier liquid (generally, distilled water is used) through the reaction coil to the sensors to form a stable, continuous, single main analysis path so that the system is ready at all times to receive samples and analyze the samples promptly. Analysis including several measurement items is carried out by connecting the metered sample zone to the center of the reagent transport pipe and connecting the sample zone so as to form a reagent zone interleaving the sample zone in series to the main analysis path, thereby introducing the sample and reagent are introduced into the main analysis path. Thus, analysis of several items are carried out by introducing the sample and reagents sequentially at a constant time interval.

Figure 3:
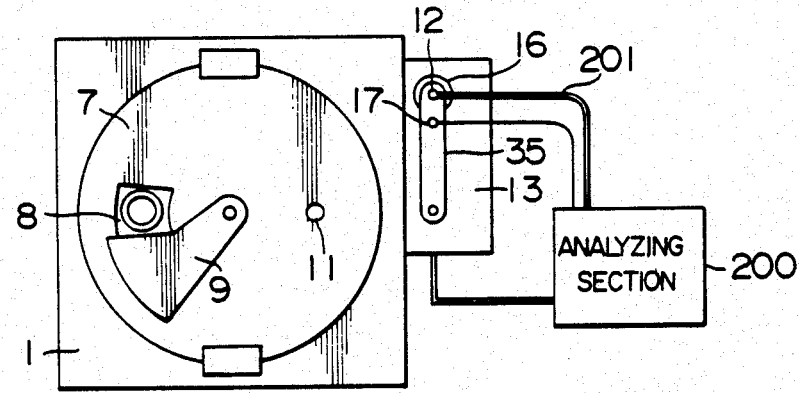
Figure 4:
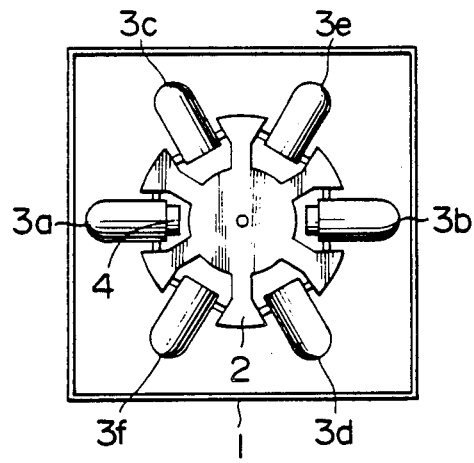

In FIGS. 2 and 3, the rotor 2 of the centrifugal separator 1 has a plurality (preferably, an even number) of pot holders 3a–3f. These pot holders are attached to the rotor 2 so that they take a vertical attitude when the rotor 2 is stationary and they swing to take a horizontal attitude as shown in FIG. 4 when the rotor 2 rotates at a high speed. The rotor 2 is connected to a driving device 5 through turning shaft 30. The driving device 5 can rotate the rotor 2 at a high speed ranging 2000–4000 R.P.M. and also can rotate the rotor 2 intermittently at a low speed so as to bring an pot holder to a desired position. The turning shaft 30 has a disk 31, on which are formed a plurality of light conducting slits corresponding to the positions of the pot holders 3a–3f. A photocoupler 6 is provided to detect the presence of a slit on the disk 31, and the electric signal produced by the photocoupler 6 is sent to the controller so that the position of each pot holder is recognized. Thus, the disk 31 and photocoupler 6 constitute a device for detecting the position of each holder.

Above the rotor 2, there is provided a cover 7, on which are formed a sample pot insertion hole 8 and an aperture 11 for taking out the sample pumping or take out pipe as will be well understood in FIG. 3. The pot insertion home 8 is used to set a sample pot 4 in a pot holder and also take out a sample pot. The pot insertion hole 8 is located at the pot setting position, and it is closed by a lid 9 during the centrifugal separating operation. The lid 9 is opened or closed automatically by a motor 10 in accordance with the command issued by the controller which is not shown in the figure.

The sample take out pipe 12 is made of metal and it is connected to a sample transfer pipe 201. The sample pipe 12 is connected electrically to an electrical conduction sensor which is not shown in the figure. A driving device 13 is provided for moving the pipe 12 and a liquid level sensing electrode 17 by moving its arm 35 vertically and rotating it horizontally. The aperture 11 is located at the sample pumping position. When the sample is pumped up after the centrifugal separating operation, the pipe 12 and electrode 17 are lowered into the sample pot, and blood plasma which is the supernatant liquid of blood is pumped and transported through the pipe 12 toward the analyzing section 200.

Each time a sample pot is positioned at the sample position and blood plasma in the sample pot is transported to the analyzing section, the pumping pipe 12 is moved vertically and horizontally so that it is transferred into a washing tube 16 as shown in FIG. 3 where the pipe is washed in the washing liquid. During the washing process, the analyzing section 200 sends distilled water to the pipe 12 so that the residue of sample within the transfer pipe 201 and pipe 12 is evacuated through the end of the pumping pipe 12. In this process, the exterior wall of the pipe 12 is also washed at the same time. Distilled water is supplied to the washing tub 16 by means of a pump 231 shown in FIG. 1.

The electrode 17 which is moved together with the pipe 12 is connected through a lead wire 37 to the electric conduction sensor which is not shown in the figure. When the pipe 12 and electrode 17 are lowered into the liquid in the sample pot, an electrical conduction is made between them and a conduction signal is issued. In this way, the quantity of the sample can be known, and the amount of pump-up liquid can be controlled by measuring the falling level of the liquid during the pumping process.

The following will describe the operation of the sampling section 100.

First, a case of processing only one sample in a hurry will be described. The sample is collected using a vacuum sampling tube containing the anticoagulant, and the sampling tube is directly used as the sample pot 4. When the sample setting key 19 on the operator's panel 18 is pressed, the lid 9 is opened. The rotor 2 has rotated in advance automatically so that a specified pot holder 3 (e.g., holder 1 in FIG. 5) is positioned at the sample insertion hole 8. Then, the operator inserts the sample pot to the specified holder. The holder number is displayed on the display panel 20. When the start key 21 is pressed, the lid 9 is closed and the rotor 2 rotates at a high speed and performs centrifugal separation. Subsequently, the rotor 2 rotates intermittently at a low speed so as to place the sample pot at the position of the sample pumping port 11, and the analytical operation for transferring blood plasma which is the separated supernatant liquid into the analyzing section 200. The result of component measurement is printed on a printer or the like. All of these operations are carried out automatically. The start key 21 has a lamp integrated therein, and the lamp lights up during the operation of the centrifugal machine, and after the separated sample has been transferred into the analyzing section and the sample pot has been returned to the sample pot insertion position, the lamp goes off to indicate the end of preprocessing. When the sample pot removal key 22 is pressed, the lid 9 of the sample pot insertion hole 8 opens, allowing the operator to take out the sample pot 4. The halt key 23 is used to close the lid 9 and terminate the operation of the centrifugal machine.

In order to meet the demand for a quick analysis in an urgent situation, this apparatus is designed to perform the centrifugal process and analysis in a short time. In particular, centrifugal separation is carried out at 4000 R.P.M. so that blood plasma can be separated in approximately two minutes including the acceleration and deceleration periods. The analyzer is capable of analyzing automatically a plurality of items needed for the urgent inspection (e.g., six items of total protein, bilirubin, creatinine, GOT, GPT, and amylase) within a period of 2 to 5 minutes including the chemical reaction. Accordingly, the result of analysis can be obtained few minutes after the operator has entered the blood sample into the apparatus.

Next, the batch process for a plurality of samples according to this embodiment will be described.

Figure 5:
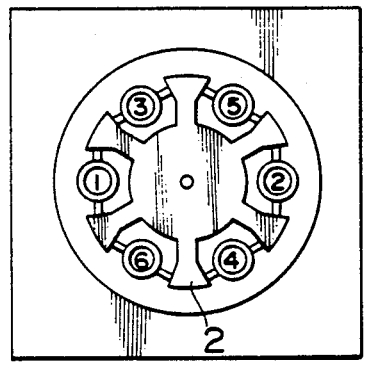

First, the lid 9 is opened by pressing the sample setting key 19, then the first sample pot is inserted as in the case of the single sample operation. When the sample setting key 19 is pressed again, the centrifugal rotor 2 is turned and holder No. 2 shown in FIG. 5 is brought to the sample insertion hole 8, and the next sample pot 4 is inserted. In this way, the operator presses the key 19 and sets sample pots in the order of No. 3, No. 4, No. 5, and No. 6 as shown in FIG. 5. Samples are disposed in pair of symmetrical positions with respect to the center of the rotor so that the rotor is closely balanced normally irrespective of the number of sample pots, with an exception of an unbalanced pot in cases of an odd number of pots.

After sample pots have been set, the centrifugal separating operation and the transfer of samples into the analyzing section are carried out. In transferring the samples into the analyzing section, the rotor 2 is turned and the samples are pumped in the same order as in the pot setting operation. When sample pots are removed from the holders by pressing the sample removal key 22, the balance of rotor and the order of analysis need not be considered, and the apparatus is designed to turn the centrifugal rotor 2 step by step in the order of No. 3, No. 5, No. 2, No. 4, and No. 6 as shown in FIG. 5 so that all sample pots are removed in a short time.

The following will describe the analyzing section 200 with reference to FIG. 1. A switching valve 202 has a slide valve 38 provided with a single metering tube 203, and fixed valves 39a and 39b. For example, if a sample is subjected to analysis for four items, the sample liquid in a quantity for at least four items is pumped up through the tube 12 into the sample transfer pipe 201. A certain amount of sample which has been pumped for the first item is introduced into the metering tube 203, and the remaining portion is held within the sample transfer pipe 201. A pump 206 is operated for pumping up the sample liquid.

The reagent liquid for each analytical item is selected from reagent reservoirs 209–212 by a flow path switching valve 240, in which a path 41 of a movable valve 40 moves to select one of reagents. The reagent which has been introduced into the reagent transfer pipe 208 by the pump 213 moves in the slide valve 38 in which the metering tube 203 contains the sample liquid, so that the sample liquid is interleaved with the reagent. The flow path switching valve 250 operates to introduce the sample liquid and reagent into the main analytical flow path 218. Distilled water from the distilled water reservoir 220 is pumped by the pump 219 throughout the flow path switching valve 250, and transported through a reaction coil 222 in a reaction tub 221 to a flow cell 224 in a photometer 223. Reference numbers 225 and 226 denote waste liquid tanks.

The reaction coil 222 is maintained at a specified temperature (e.g., 37° C.) necessary for the color development reaction. While the sample and reagent introduced in the main flow path 218 go through the reaction coil, the color development reaction proceeds, then the sample and reagent flow into the flow cell 224 and the concentration of analytical components is measured by the photometer 223. For a measurement means, it is possible to use so-called "end-point" method in which the end of color development is measured while the color-developing sample goes through the flow cell 224. However, as a quick process method, it is effective to use so-called "rate assay" method in which the introduced sample is stopped temporarily in the flow cell and the reaction speed is measured. These methods can be used selectively depending on the item of analysis. Pinch valves 227 and 228 are used to stop the sample in the flow cell and bypass the following flow.

The flow path switching valve 240 connects to one of sample bottles 209, 210, 211 or 212 when it is set so that the flow path 41 moves by two steps in the direction shown by the arrow, and it connects to the distilled water feed path 250 so as to wash the sample transfer path when it is set to the intermediate position. That is, the flow path is washed before the kind of reagent is changed.

At a time when the sample and reagent for the first analysis flow completely into the main analytical flow path 218, the switching valve 202 is switched to place the clean flow path 205 at the position of the metering tube 203, then the pump 206 operates to introduce a certain amount of sample for the second analysis from the sample transfer pipe 201 to the position of the metering tube 203. At the same time, the reagent switching valve 240 is switched so that the reagent for the second analysis is introduced into the reagent transfer pipe 208. Subsequently, the valve 202 is switched and the metering tube 203 containing the sample is moved to the position of the flow path 204 so as to connect the metering tube to the reagent transfer pipe 208. Then, the pump 219 is operated to transfer the sample and reagent toward the reaction coil 222, and the second analysis is carried out. In this way, the third and fourth analyses are carried out continuously.

According to this embodiment, the operations from the setting of the sample pot to the pumping of the sample into the transfer pipe 201 complete in two minutes when the sample is analyzed for four items. In this embodiment, after the sample pot has been set, the operations from the separation of blood plasma by the centrifugal operation to the pumping of the sample into the sample retaining tube complete in two minutes, then the sample and reagent are introduced for metering into the main analytical flow path at an interval of 30 seconds. It takes two mintues for analyzing one item, and in the remaining 20 seconds within this period, the sample and reagent are held in the flow cell so that the measurement of reaction is carried out.

According to this embodiment, it takes 5 to 6 minutes for the operations from the setting of the sample pot to the end of analysis for four items, and two minutes after the sample pot has been set, the analysis for the next sample can be started.

This system is capable of analyzing blood for almost all items necessary for the clinical inspection such as biochemical components, total protein, blood sugar, GOT, GPT, cereatinine, and cholesterol. The vacuum tube or vactena tube for collecting blood can conveniently be used directly as a sample pot.

According to this embodiment, the analytical processes for the inspection of chemical components of a sample starting with the centrifugal separation and ending with the analysis can be carried out merely by entering the sample of whole blood of a patient collected in the vactena tube into the apparatus without the need of a specifically skilled personal such as a clinical inspector.

Another embodiment of the present invention will be described with reference to FIGS. 6 and 7. In the new embodiment, constituents having the same functions as those of the precious embodiment shown in FIG. 1 are referred to with the common reference numbers.

Controller 150 incorporates a microcomputer, and is connected to the operator's panel 18, analyzing section 200, data processor 160, printer 170, CRT display 180, and liquid level sensing electrode 17. The controller 150 operates to control the pumping pipe driver 13, photocoupler 6, stepping motor 130, rotary solenoid 136, high-speed motor 105, lifting mechanism 125, pot detector 127, and rotary solenoid 110.

First, a plurality of sample pots containing blood collected from patients in the hospital are prepared. When the operator presses the setting key 19 on the control panel 18, the rotary solenoid 110 operates to turn the lid 109 as shown in FIG. 7, and the sample pot insertion hole 8 is opened. Then, a pot holder 103a which has been positioned to the sample setting position is lifted. The pot holder lifting mechanism 125 has a rack 51 and pinion 52. The rack 51 has a contact member 50 at its end, and the operation of the contact member facilitates the setting of the sample pot 4. When the operator sets a sample pot through the hole 8 and presses the rotor feed key 45, the pot holder 103a is lowered. At this time, the pot detector 127 located in the vicinity of the lid 109 responds to the presence of a pot and issues a signal to the controller 150. Then, the rotor 102 is turned at a low speed by the intermittent feed motor 130, and a pot holder 103b which will be the second holder is placed at the sample setting position as in the case shown in FIG. 5. The pot holder 103b located symmetrically to the pot holder 103a is subsequently lifted by the lifting mechanism 125.

When the operator sets the second sample pot through the hole 8 into the holder 103b and presses the rotor feed key 45, the pot holder 103b comes down and the rotor 102 rotates at a low speed, then the next holder is placed at the setting position. In this way, sample pots are set in the order for maintaining the balance of the rotor. After all pots have been set in the pot holders, the operator presses the start key 21.

In response to the signal from the start key 21, the controller 150 closes the lid 109 and operates the rotor 102 at a high speed for a predetermined period. The appropriate rotor speed for centrifugal separation is around 4000 R.P.M. The centrifugal operation takes one minute and the acceleration and deceleration take 20 seconds each, and blood plasma is separated from blood in a total time of 1 minute and 40 seconds. The rotor used in this embodiment maintains the holders at a slant angle of 45° during the centrifugal separating operation. When the high-speed rotation starts, a member 45 on the holder comes into contact with the slant section 43 of the rotor, and each holder does not swing over the critical angle of 45° as shown by the dashed line. Thus, by using the slant portion of the interior wall of the sample pot, separation of blood into two layers by the centrifugal force is further advanced.

The rotor 102 has a friction plate 140 formed thereon, which is connected through another friction plate 134 to a low-speed drive mechanism 132. As shown in FIGS. 6 and 7, when the rotor rotates intermittently at a low speed, the rotary solenoid 136 moves the lever mechanism 138 to bring the friction plate 134 into contact with the friction plate 140 on the rotor so that the rotation of the stepping motor 130 is transmitted to the rotor. When the rotor rotates at a high speed, the stepping motor 130 does not operate, and the friction plates 134 and 140 are apart from each other. When the rotor rotates at a low speed, a position sensor having a photocoupler 6 and rotary disk 31 operates to assist the accurate positioning of each pot holder.

Upon expiration of the separating period, the rotor 102 is decelerated and stopped temporarily. Then, the rotor is driven at a low speed by the stepping motor 130, and holders are positioned intermittently to the sample pumping position registering with the pumping pipe insertion hole 11. While each pot holder is stationary at the sample pumping position, the sample pumping operation is carried out. That is, the pipe 12 lowered through the hole 11 by the driver 13 and the tip of the pipe 12 is plunged into blood plasma in the pot 4. The liquid level sensing electrode 17 detects the depth of plunge of the pipe and halts the lowering operation by the driver 13.

It takes 20 seconds or less for introducing the sample liquid. The sample liquid pumped through the pipe 12 is subjected to the component measurement in the similar flow system to that of the analyzing section 200 as described in connection with FIG. 1. The introduced sample is added with a reagent depending on the item of analysis, and a chemical reaction specific to its components will proceed. The reactive liquid is exposed to the light in the photometer so that the absorbed luminous intensity at specific wavelengths is measured. Basing on this measurement, the concentration of each component is calculated by the data processor 160, and the result of analysis is displayed on the CRT display 180 and printed on the printer 170.

We claim:

1. A method for clinical analysis comprising the steps of:
   (a) rotating a rotor intermittently at a low speed to adjust each of a plurality of container holders connected to said rotor at a first position and inserting a sample container containing whole blood therein in one of said container holders;
   (b) rotating said rotor at a high speed so as to direct the bottom of each of said sample containers outward centrifugally to separate the whole blood contained in said sample containers;
   (c) rotating said rotor intermittently at a low speed to adjust repetitively each of said sample containers at a second position for taking-out a portion of the separated whole blood;
   (d) inserting a liquid take-out pipe into a layer in the separated whole blood in each of said sample containers to take-out a sample portion of the separated whole blood while said sample container held in said container holder is placed at said take-out position; and
   (e) measuring the sample introduced into the analyzing section through said liquid take-out pipe in accordance with an item of analysis.

2. A method for clinical analysis according to claim 1 comprising a step of introducing a plurality of analytical items into said liquid take-out pipe while each of said sample containers stays at said sample take-out position.

3. A method for clinical analysis according to claim 1 comprising a step of positioning said container holders sequentially to said first position after sample liquids have been taken out by said liquid take-out pipe, and lifting each positioned sample container.

4. A method for clinical analysis according to claim 1, comprising the steps of introducing a reagent into a flow path while a sample liquid is transported in said flow path, and introducing a reactive liquid into a flow cell within a photometer.

5. A method for clinical analysis according to claim 1, wherein said sample containers are kept substantially horizontal during said high speed rotation and substantially vertical during said low speed rotation.

6. A clinical analyzer comprising:
a sampling section having a sample liquid take-out means and a centrifugal separation means, said centrifugal separation means having a rotor provided with a plurality of container holders in which sample containers can be held, said centrifugal separation means having a drive means for successively rotating said rotor intermittently so that each container holder stops temporarily at a container setting position such that a sample container can be fed into a sample holder, rotating said rotor continuously at a high speed during a centrifugal separating operation of the sample within a sample container, and moving said rotor intermittently at a low speed so that each container holder stops temporarily at a sample take-out position during a sample take-out operation,
an analyzing section which measures an introduced liquid sample in accordance with an item of analysis,
means defining a flow path between the sampling section and the analyzing section, wherein
said sample liquid take-out means operates to take out sample liquid in a container holder positioned at said sample take-out position and to introduce said liquid toward said analyzing section, and said analyzing section comprises means for mixing a sample liquid introduced through the take-out means with a reagent inside the flow path, and a photometer for measuring a mixed liquid.

7. A clinical analyzer according to claim 6, comprising a flow cell in the analyzing section, and means for introducing a sample for a plurality of different items into the flow cell in doses at spaced intervals.

8. A clinical analyzer according to claim 6, further comprising:
means for lifting said container holder when the sample container on said container holder is in a position to remove the sample container after taking-out a sample therefrom.

9. A clinical analyzer comprising an analyzing section which measures an introduced liquid sample in accordance with an item of analysis; and a sampling section having a sample liquid take-out means and means for centrifugal separation, said centrifugal separation means having a rotor provided with a plurality of container holders in which sample containers can be set, said centrifugal separation means having a drive means for moving said rotor intermittently so that each of said container holder stops at a container setting position during a sample setting operation, for rotating said rotor at a high speed during a centrifugal separation operation, and for moving said rotor intermittently so that each of said container holders stops temporarily at a sample take-out position during a sample take-out operation, said centrifugal separation means having a holder position detector which detects the position of each container holder and halts the operation of said rotor, said sample liquid take-out means operating to take out sample liquid in a container holder positioned at said sample take-out position and introduce said liquid toward said analyzing section.

10. A clinical analyzer according to claim 9, wherein said sample take-out pipe has an associated liquid level sensing electrode.

11. A clinical analizer according to claim 9 comprising a means for lifting a sample container set in a container holder when said container holder is positioned at a container take-out position.

12. A clinical analyzer according to claim 9, wherein means is provided to keep container holders in which sample containers are set in a slant attitude when said rotor rotates at high speed.

13. A clinical analyzer according to claim 9, wherein said drive means is provided for positioning, subsequently to the positioning for a first container holder, a second container holder located at a position symmetrically opposite to a position of said first container holder with respect to the center of rotation to said container setting position.

14. A clinical analyzer according to claim 9, wherein said centrifugal separation means has a means for covering said rotor, said cover means being provided therein with a first aperture at said container setting position for transferring a sample container, and a second aperture at said sample take-out position for inserting a sample take-out pipe.

15. A clinical analyzer according to claim 14 comprising a lid means which is open when a sample container is set on said container holder and closes said first aperture when said rotor rotates at a high speed.

16. A method for clinical analysis wherein a rotor having therein a plurality of container holders is kept at a predetermined position comprising:
(a) a first step of rotating said rotor intermittently to position each of a plurality of empty container holders at an inserting position so as to insert each of a plurality of said sample containers containing whole blood therein,
(b) a second step of rotating said rotor at a high speed to centrifugally separate said whole blood contained in said sample containers into blood clot and blood serum,
(c) a third step of rotating said rotor to position said container holders each holding one of said sample containers including the blood clot and the blood serum at an aspirating position so as to aspirate the blood serum from said sample containers, and
(d) a fourth step of rotating said rotor intermittently to position each of said container holders at said inserting position for taking to said sample containers including the blood clot from said container holders, wherein the blood serum aspirated in said third step is led through a take-out pipe inserted into said respective sample containers into a flow cell of an analyzing section.

17. A method for clinical analysis according to claim 16, wherein the positioning operation of said third step and the positioning operation of said fourth step are synchronized.

18. A method for clinical analysis according to claim 16, wherein reagent is added to the blood serum in a flow conduit provided between said take-out pipe and said flow cell.

19. A method for clinical analysis wherein a rotor having therein a plurality of container holders is kept at a predetermined position, comprising:
   (a) a first step of rotating said rotor intermittently to position each of a plurality of empty container holders at an inserting position so as to insert each of said sample containers containing whole blood therein,
   (b) a second step of rotating said rotor at a high speed to centrifugally separate said whole blood contained in said sample containers into blood clot and blood serum,
   (c) a third step of rotating said rotor to position said container holders each holding one of said sample containers including the blood clot and the blood serum at an aspirating position so as to aspirate the blood serum from said sample containers, and
   (d) a fourth step of rotating said rotor intermittently to position each of said container holders at said inserting position for taking out said sample containers including the blood clot from said container holders, wherein each of said sample containers are rotated to said inserting position so as to be inserted in turn in each of said container holders in an order for forming a pair thereof located in a substantially opposite direction with respect to the center of said rotor, and the blood serum aspirated in said third step is led through a take-out pipe inserted into said respective sample containers into a flow cell of an analyzing section.

20. A clinical analyzer comprising:
   (a) a rotor means having a rotor and a plurality of container holders arranged on said rotor,
   (b) means for intermittently rotating said rotor in a first mode to successively position each of a plurality of empty container holders at a single inserting position so as to insert a sample container containing whole blood therein into each of said container holders so as to be located in turn in a substantially opposite position with respect to the center of said rotor,
   (c) means for inserting a take-out pipe into said sample container held in said container holder located at said aspirating position in said third mode so as to aspirate blood serum separated from said whole blood in said sample container into said take-out pipe,
   (d) cover means having a container aperture for inserting therethrough said sample container at said inserting position and a pipe aperture for inserting therethrough said take-out pipe for covering said rotor, and
   (e) flow cell means for measuring said blood serum which has flowed through said take-out pipe.

21. A clinical analyzer according to claim 20, further comprising:
   flow conduit means for connecting said take-out pipe with said flow cell, and
   reagent means for leading reagent through a switching valve into said flow conduit means.

22. A clinical analyzer according to claim 20, further comprising:
   lid means for closing said container aperture, and
   means for activating said lid means to close said container aperture in said second mode and to open said container aperture in said first and fourth modes.

23. A clinical analyzer comprising:
   (a) rotor means having a rotor and a plurality of container holders arranged on said rotor and provided in an analyzer for conducting a first mode intermittently rotating said rotor to successively position each of a plurality of empty container holders at a single inserting position so as to insert each of said sample containers containing whole blood therein into each of said sample containers, a second mode rotating said rotor at a high speed to centrifugally separate said whole blood contained in said sample containers, a third mode rotating said rotor intermittently to position said container holders at an aspirating position, and a fourth mode rotating said rotor intermittently to position each of said container holders at said inserting position for taking out said sample containers,
   (b) means for inserting a take-out pipe into said sample container held in said container holder located at said aspirating position in said third mode so as to aspirate blood serum separated from said whole blood in said sample container into said take-up pipe,
   (c) cover means having a container aperture of inserting therethrough said sample container at said inserting position and a pipe aperture of inserting therethrough said take-out pipe for covering said rotor,
   (d) means for lifting said sample container held in said container holder indexed in said inserting position so as to project an upper portion of said lifted sample container over said container aperture of said cover means, and
   (e) an analyzing means for measuring said blood serum which has flowed through said take-out pipe.

* * * * *